(12) United States Patent
Pigamo et al.

(10) Patent No.: US 11,286,223 B2
(45) Date of Patent: Mar. 29, 2022

(54) METHOD TO PURIFY A CRUDE STREAM CONTAINING HYDROCHLOROFLUOROOLEFIN

(71) Applicant: Arkema Inc., King of Prussia, PA (US)

(72) Inventors: Anne M. Pigamo, Francheville (FR); Kevin Hisler, Chaponnay (FR); Wayne Brooks, Paducah, KY (US); Jay F. Miller, Downingtown, PA (US); Bertrand Louis Maurice Collier, Montbard (FR); Emmanuel D. Boussarie, Decines Charpieu (FR)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 17/293,639

(22) PCT Filed: Oct. 10, 2019

(86) PCT No.: PCT/US2019/055553
§ 371 (c)(1),
(2) Date: May 13, 2021

(87) PCT Pub. No.: WO2020/101825
PCT Pub. Date: May 22, 2020

(65) Prior Publication Data
US 2022/0009859 A1    Jan. 13, 2022

Related U.S. Application Data

(60) Provisional application No. 62/767,527, filed on Nov. 15, 2018.

(51) Int. Cl.
*C07C 17/395* (2006.01)
*C07C 17/42* (2006.01)
*C07C 17/383* (2006.01)

(52) U.S. Cl.
CPC ......... *C07C 17/395* (2013.01); *C07C 17/383* (2013.01); *C07C 17/42* (2013.01)

(58) Field of Classification Search
CPC ...... C07C 17/395; C07C 17/42; C07C 17/383
See application file for complete search history.

(56) References Cited

U.S. PATENT DOCUMENTS

| 8,987,534 | B2 | 3/2015 | Elsheikh et al. |
| 9,061,958 | B2 | 6/2015 | Wismer et al. |
| 9,221,732 | B2 | 12/2015 | Okamoto et al. |
| 9,272,968 | B2 | 3/2016 | Kopkalli et al. |

(Continued)

*Primary Examiner* — Jafar F Parsa
(74) *Attorney, Agent, or Firm* — Steven D. Boyd

(57) ABSTRACT

Disclosed is a method of purifying a stream of crude hydrochlorofluoroolefin refrigerant produced by the reaction of 1,1,3,3 tetrachloropropene (R1230za) or 1,1,1,3,3-pentachloropropane (R240fa) with HF. The process includes a step of removing the cis-(Z) isomer by distillation of the crude refrigerant stream prior to a step of reacting the crude refrigerant stream with a base. The reaction with the base is a necessary step in production of the refrigerant and is done to remove HF and residual HCl from the crude refrigerant stream. Removal of the cis-(Z) isomer before the reaction with the base reduces the amount of toxic flammable trifluoropropyne (TFP) that is produced as a side-reaction during the reaction with the base. In addition, temperature control during the reaction with the base is less critical to minimizing the TFP production if the cis-(Z) isomer is first removed.

15 Claims, 1 Drawing Sheet

(56) References Cited

U.S. PATENT DOCUMENTS

| | | |
|---|---|---|
| 9,540,296 B2 | 1/2017 | Chiu et al. |
| 2012/0261252 A1 | 10/2012 | Knapp |
| 2013/0158305 A1 | 6/2013 | Takahashi |
| 2014/0020691 A1 | 7/2014 | Pokrovski et al. |
| 2017/0081265 A1 | 3/2017 | Chiu et al. |

METHOD TO PURIFY A CRUDE STREAM CONTAINING HYDROCHLOROFLUOROOLEFIN

This present application is the national phase under 35 USC § 371 of prior PCT International Application Number PCT/US2019/055553 filed Oct. 10, 2019 which designated the United States of America and claimed priority to U.S. Provisional Patent Application Ser. No. 62/767,527 filed Nov. 15, 2018.

FIELD OF THE INVENTION

The invention relates to a step in the purification process of hydrochlorofluoroolefin refrigerants that are made from a process whereby a starting material such as 1,1,3,3 tetrachloropropene (R1230za) or 1,1,1,3,3 pentachloropropane (R240fa) is reacted with HF to produce the desired hydrochlorofluoroolefin. When making such compounds in this way, there is the need to remove small amounts of HF from an organic-rich process stream that, in addition to the desired refrigerant, may also contain small but undesirable amounts of other organic products produced as side reactions during the synthesis reaction. The inventive process first removes the undesired higher boiling cis-(Z) form of the hydrochlorofluoroolefin by distillation, then neutralizes any acid, such as HF and/or HCl, and finally recovers the desired trans-(E) form of the hydrochlorofluoroolefin which is sent to final purification. The neutralization system utilizes a basic salt of an alkali metal or alkaline earth metal such as KOH or NaOH or utilizes ammonia as a base. The base may optionally be combined with one or more reducing agents such as bisulfite, sulfite or mixtures thereof, to remove the HF and/or HCl. By first removing the undesirable cis-(Z) form prior to the neutralization step, there is an unexpected and marked decrease in unwanted by-products, particularly 3,3,3-trifluoropropyne (TFP).

BACKGROUND OF THE INVENTION

There is a continuing pressure to produce more environmentally friendly versions of refrigerants, heat transfer fluids, foam blowing agents, solvents, etc. that not only have lower ozone depleting potential, but that also do not contribute to global warming. Chlorofluorocarbons (CFC) and hydrochlorofluorocarbons (HCFC), widely used for these applications, are ozone depleting substances and are being phased out in accordance with guidelines of the Montreal Protocol. Hydrofluorocarbons (HFC) are a leading replacement for CFCs and HCFCs in many applications; although they are safe for the ozone layer they still generally possess high global warming potential and for that reason there is increasing need to minimize their use as well.

One class of compounds that has been identified to replace ozone depleting and high global warming substances are halogenated olefins, such as hydrofluoroolefins (HFO) and hydrochlorofluoroolefins (HCFO). The HFOs and HCFOs provide the low global warming potential and zero or near zero ozone depletion properties desired. An exemplary such HCFO is R1233zd-E, trans (E) 1-chloro-3,3,3, trifluoro-2-propene.

A typical process for producing R1233zd-E is the reaction of 1,1,3,3 tetrachloropropene (R1230za) or 1,1,1,3,3 pentachloropropane (R240fa) with HF. An example of such a process is described in U.S. Pat. No. 9,061,958 which is incorporated by reference in its entirety herein for all purposes.

The hydrofluorination reaction can be done in the gas or the liquid phase using any reactor known in the art. Non-limiting examples include a tubular reactor, plug flow reactor, stirred tank reactor, or un-stirred tank reactor. The reaction may be catalyzed with a homogeneous or heterogeneous catalyst, or the reaction can be run without a catalyst. The product of the reaction can be distilled, in either a distillation column or partial column such as a rectification column, to remove light products and recover heavier reactants and intermediates to recycle back to the reactor. The light products from the reactor will contain organics, HCl and HF that was either carried overhead in the distillation column by the normal operation of the column or taken overhead as part of an organic-HF azeotrope.

Generally the next step is removal of the HCl by distillation. Trace amounts of HCl may remain in the bottom stream. The HCl stream is considered a product stream wherein the HCl may optionally be further purified and/or diluted with water for sale.

The bottoms stream is then sent to a separator to remove most of the HF from the organics. This separations step may be distillation, extraction, adsorption, or preferably by use of a decanter. When using a decanter, the HF-rich phase may contain between 20 and 40 weight % organics. This stream can optionally be sent to a distillation column to remove the organics, or organic-HF azeotropes. The HF is sent back to the reactor and the organic-rich stream sent back to the decanter.

The organic rich stream from the separator, i.e., the bottoms stream from a decanter, contains some HF, typically between 0.1 and 6 wt %. There is then a need to remove the HF from this stream, which is a crude mixture of the desired refrigerant and small amounts of impurities such as undesired isomers, under and over-fluorinated side products, as well as traces of the HCl that is produced as a result of the reaction.

There are a number of possibilities to recover and purify the desired refrigerant and remove the remaining HF.

To remove HF from this crude refrigerant stream, many of the current processes pass the vaporized stream through an aqueous or aqueous-basic stream in an absorber tower at high temperatures. Typically this processing is done with very volatile products to keep the temperature low enough to ensure that no unwanted side reactions take place. The first step is to pass the stream through an aqueous absorber to remove most of the HF. Then the stream passes through an absorber with a basic stream or a basic/reducing agent stream. The base in the aqueous stream reacts with HF forming a salt, which then flows with the aqueous stream and out the tails of the tower. The heads of the tower contain the HF-free refrigerant which then goes to one or more distillation towers for further purification. However, when processing crude R1233zd-E (trans-form) there is a tendency to form unwanted by-products such as 3,3,3-trifluoropropyne (TFP).

U.S. Pat. No. 9,221,732 is directed to a method of separating crude R1233zd-E containing HF and HCl. The method comprises reducing the HCl level so that the mixture phase separates. The upper layer contains most of the HF and the lower layer contains predominately R1233zd-E with low levels of HF and HCl. The HF and HCl are removed by washing the stream with an aqueous solution or an aqueous alkaline solution. There is no disclosure of further purification of the wet R1233zd-E, nor of efforts to minimize undesired by-products as a result of washing the solution with base.

U.S. Pat. No. 9,272,968 discloses a method to suppress the formation of 3,3,3-trifluoropropyne (TFP), a toxic and flammable material that can be formed due to the reaction of R1233zd with the basic solution. The disclosed process comprises a method whereby the HF is removed with water in two separate washing steps and the resulting solution is then dried with $H_2SO_4$ absorption system. In a second embodiment, the second water wash step is replaced with a washing step with a weak caustic solution (pH 7-pH 10). The resulting stream then can be dried with $H_2SO_4$. In another embodiment, rather than $H_2SO_4$, the water and trace HF are removed with a solid desiccant.

U.S. Pat. No. 9,540,296 discloses a process wherein a crude stream of R1233zd contains HCl in addition to the low level of HF. This stream is washed with an aqueous or basic solution, resulting in a wet vapor which is condensed. The resulting liquid mixture, containing HCFO-1233zd, other organics, and water, is allowed to settle, and thereafter, the lighter water layer is decanted off from the top of the mixture. The heavier HCFO-1233zd layer is then withdrawn from the bottom of the decanter to a desiccant dryer (e.g., molecular sieve, activated alumina, silica gel, and the like) to further remove the residual soluble moisture from the HCFO-1233zd to about 80 ppm or less. The disclosure does not describe a method whereby the levels of the undesired organics or TFP can be controlled by the method of effecting the washing step.

U.S. Patent Application Publ. 2013/0158305 discloses a method for removing moisture from fluorine-containing compounds. The method comprising bringing a fluorine-containing compound contaminated with moisture into contact with an aqueous solution containing a metal salt. The disclosed method can continuously and efficiently remove moisture from various fluorine-containing compounds, such as hydrofluoroolefins. The disclosure does not discuss a particular method to remove low levels of HF from the crude refrigerant stream.

U.S. Patent Application Publ. 2017/0081265 discloses separation processes that use azeotropic or azeotropic-like compositions of 1-chloro-3,3,3-trifluoropropene (HCFO-1233zd). The separation processes utilize the azeotropic or azeotropic-like properties of the compositions with various combinations of separation techniques (e.g., distillation and decanting) to purify 1-chloro-3,3,3-trifluoropropene.

There is thus a need for processes that can remove the HF from a process stream comprising crude R1233zd-E with undesired organics, without decreasing the amount of the desired R1233zd-E or creating 3,3,3-trufluoropropyne (TFP) and other undesirable organics. Additionally, there remains a need to economically remove water from the resulting HF-free refrigerant in an ecologically sensitive manner.

SUMMARY OF THE INVENTION

We have surprisingly found that when the cis (Z)-isomer R1233zd-Z is removed prior to the neutralization step, formation of the unwanted by-products, especially TFP, is reduced significantly. The process disclosed herein is not limited to production of R1233zd-E, but is applicable to all HFCOs having Z or E isomers.

We have thus found that removing the cis-(Z) form of a hydrochlorofluoroolefin from a crude stream that contains both the cis-(Z) and trans-(E) forms as well as 0.1 to 6 wt % of HF, reduces the amount of unwanted by-products produced during the subsequent neutralization step. In particular the amount of 3,3,3-trifluoropropyne (TFP) is significantly reduced.

The process disclosed herein comprises generally a step of first reducing the level of the R1233zd-Z isomer in the crude R1233zd-E stream to less than 1% by weight, preferably to less than 0.5% by weight and still more preferably to below 0.1% by weight. When the R1233zd-Z isomer is thus removed, the crude R1233zd-E stream is then combined with a basic stream (e.g. aqueous NaOH or KOH) stream, wherein the caustic stream has a pH of 13 or higher. The crude R1233zd-E stream and the basic stream are combined such that the temperature remains below 60° C., preferably less than 45° C. The basic stream converts the HF and HCl to salts, but the base does not otherwise alter the composition of the stream comprising crude R1233zd-E and organics. This combined stream then splits into two liquid phases—an organic phase comprising crude R1233zd-E and organics; and an aqueous phase comprising the salts of HF and HCl as well as any unreacted basic species.

The organic crude stream comprising the crude R1233zd-E may then be dried by conventional means, such as molecular sieves, and then can be distilled to remove light and heavy organic by-products in order to produce purified R1233zd-E that meets all product specifications. The aqueous phase may optionally be sent to a stripping column to remove and recover the trace crude R1233zd-E.

If a stripping column is used to remove trace crude R1233zd-E from the organics phase, the stripping agent can be for example steam, air or nitrogen. Preferably the stripping agent is steam. The overheads from the stripping column phase-separate into two liquid phases—a crude R1233zd-E phase and an aqueous phase. The aqueous phase is sent back to the stripper column or can be sent to waste treatment. The aqueous stream contains only trace amounts of organics and can therefore be disposed of easily.

Within this specification, embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Various non-limiting aspects of the invention may be summarized as follows:

Aspect 1: A method for the removal of an acid, wherein the acid comprises at least one of HF or HCl, from a crude stream of a hydrochlorofluoroolefin (HFCO) wherein the HFCO comprises at least one E isomer and at least one corresponding Z isomer, wherein the method comprises the steps of:

a) reducing the amount of one of the E isomer or the corresponding Z isomer in the crude stream of an HFCO to produce a reduced isomer crude HFCO stream;

b) contacting the reduced isomer crude HFCO stream with an aqueous base stream, wherein step b) takes place at a reaction temperature;

whereby the base reacts with the at least one of HF or HCl forming a salt, whereby the removal of at least one of HF or HCl is accomplished by removal of the salt and wherein step b) produces a reduced isomer reduced acid crude HFCO stream and a basic aqueous trace crude HFCO stream comprising the salt;

wherein step a) is performed prior to step b).

Aspect 2: The method according to aspect 1, wherein the crude stream of a hydrochlorofluoroolefin comprises E (trans)-1,1,1-trifluoro-3-chloro-2-propene and Z (cis)-1,1,1-trifluoro-3-chloro-2-propene and the step a) comprises reducing the amount of Z (cis)-1,1,1-trifluoro-3-chloro-2-propene in the crude stream of the hydrochlorofluoroolefin.

Aspect 3: The method according to aspect 1 or aspect 2, wherein step a) comprises a step of distillation.

Aspect 4: The method according to any of aspects 1-3, wherein the aqueous base stream has a pH of at least 13.5.

Aspect 5: The method according to any of aspects 1-4, wherein the aqueous base stream comprises at least 5 weight % aqueous KOH or at least 5 weight % NaOH.

Aspect 6: The method according to any of aspects 1-5, wherein the reaction temperature is 50° C. or less.

Aspect 7: The method according to in any of aspects 1-6, wherein the reaction temperature is 30° C. or less.

Aspect 8: The method according to any of aspects 1-7, further comprising a step c), wherein step c) is performed after step a) and prior to step b); wherein step c) comprises a step of contacting the reduced isomer crude HFCO stream with a water stream whereby the water stream dissolves the at least one of HF or HCl, whereby partial removal of at least one of HF or HCl is accomplished, wherein step c) produces an aqueous HF/HCl/trace crude HFCO stream and a reduced acid crude HFCO stream and wherein the reduced acid crude HFCO stream is fed to step b) and wherein step c) takes place at a washing temperature.

Aspect 9: The method according to any of aspects 1-8, wherein the method further comprises a step d) wherein step d) is accomplished after step b), and wherein the step d) comprises a step of removing trace crude HFCO from the basic aqueous trace crude HFCO stream emerging from step b).

Aspect 10: The method according to aspect 9, wherein step d) comprises stripping using a stripping agent and wherein the stripping agent is selected from the group consisting of air, nitrogen, and steam.

Aspect 11: The method according to aspect 10, wherein the stripping agent comprises steam.

Aspect 12: The method according to aspect 8, wherein the method further comprises a step e) wherein the step e) is accomplished after step b) and after step c), and wherein step e) comprises i) combining the basic aqueous trace crude HFCO stream emerging from step b) with the aqueous HF/HCl/trace crude HFCO stream emerging from step c) to produce a combined aqueous trace crude HFCO stream and ii) removing trace crude HFCO from the combined aqueous trace crude HFCO stream.

Aspect 13: The method according to aspect 12, wherein ii) comprises stripping using a stripping agent and wherein the stripping agent is selected from the group consisting of air, nitrogen, and steam.

Aspect 14: The method according to aspect 13, wherein the stripping agent comprises steam.

Aspect 15: The method according to any of aspects 1-14, wherein the reduced isomer reduced acid crude HFCO stream emerging from step b) comprises less than 3000 μmol/mol of 3,3,3-trifluoropropyne.

DETAILED DESCRIPTION OF THE INVENTION

The nomenclature used to refer to various chemical compounds (including refrigerants) discussed herein is as follows:

Crude R1233zd-E or R1233zd-E crude means a stream containing mostly R1233zd-E isomer, but also named and unnamed contaminants, including possibly the R-1233zd-Z isomer that has not been fully purified and does not meet the specifications for a pure product.

R1233zd-E: trans-1,1,1-trifluoro-3-chloro-2-propene
R1233zd-Z: cis-1,1,1-trifluoro-3-chloro-2-propene
TFP: 3,3,3-trifluoropropyne
R1234ze-E: trans-1,3,3,3-tetrafluoro-2-propene
R1234ze-Z: trans-1,3,3,3-tetrafluoro-2-propene
R1230za: 1,1,3,3-tetrachloro-2-propene
R240fa: 1,1,1,3,3-pentachloropropane It should be understood that while the examples disclosed herein describe the exemplary purification of crude R1233zd-E, that other halogenated propene compounds are likewise suitable to be processed in the same way. Non-limiting examples of compounds that can be purified using the inventive process are: monochloro-trifluoropropenes such as trans-1,1,1-trifluoro-3-chloro-2-propene; cis-1,1,1-trifluoro-3-chloro-2-propene.

When the refrigerant R1233zd-E is produced, one possible process route is to convert either R240fa or R1230za into R1233zd-E by a reaction with HF. The liberated HCl is removed and the resulting stream is sent to a decanter. The decanter operation is described in U.S. Pat. No. 8,735,636, which is incorporated by reference herein in its entirety for all purposes. The top HF-rich phase from the decanter is sent directly, or optionally, through an azeotrope column, to recycle the excess HF back to the reactor that produces the R1233zd-E. The bottom organic-rich phase from the decanter, containing mostly crude R1233zd-E, with about 0.1 to 6 weight percent HF, is sent for further purification.

As discussed above, in order to purify crude R1233zd-E it is necessary to remove the HF and residual HCl. This is best done by reacting the crude R1233zd-E with a base and has been discussed in U.S. Pat. No. 9,061,958 which mentions the removal of HF from crude R1233zd-E solutions by "water, aqueous NaOH, aqueous KOH and mixtures thereof." However, when crude R1233zd-E mixtures are reacted with solutions having a pH greater than 10, undesirable by-products, mostly TFP, are produced.

A method to overcome the problem of TFP formation is to distill R1233zd-Z out of the crude R1233zd-E mixture of both isomers before the neutralization step. Unexpectedly, this reduces TFP production significantly.

Figure 1:
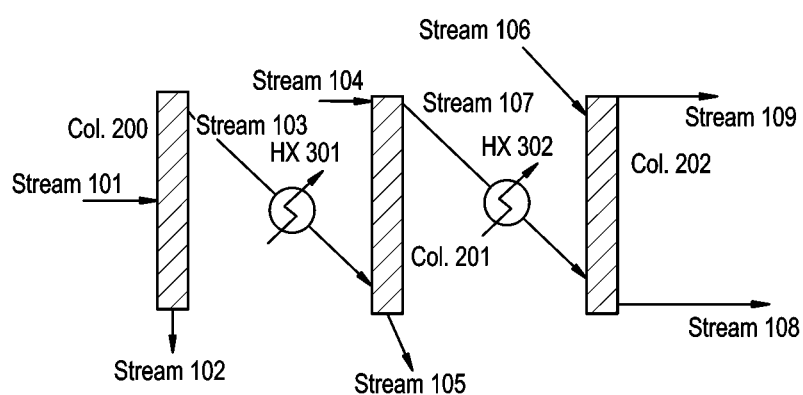
FIG. 1 shows an embodiment of the process according to the invention.

The following description of a first embodiment refers to the block process diagram in FIG. 1.

FIG. 1 shows the crude R1233zd-E stream 101 which contains from 0.1 to 6 wt % HF, as well as possibly some HCl. The amount of HF and the temperature of this stream depends on the prior processing steps to produce the stream 101. The temperature can range from −60° C. to 50° C. For example, if the prior processing step is a decantation, the decanter may be run from −40 to 50° C. The organic in stream 101 typically contains 50-99%, 70-97%, 80-96% R1233zd-E with between 40-1%, 30-3%, 20-4% of the organic content comprising R1233zd-Z. Stream 101 is sent to distillation column 200 where it is distilled to remove the R1233zd-Z isomer from the desired R1233zd-E isomer. Distillation column 200 removes the unwanted R1233zd-Z isomer out a bottoms stream 102. Stream 103 is the vapor overheads from column 200 containing the crude R1233zd-E and less than 0.1% R1233zd-Z, which is then taken to an optional heat exchanger 301. Heat exchanger 301 can serve to cool the crude R1233zd-E vapor stream 103, but stream 103 still remains as a vapor, or heat exchanger 301 can heat the stream to ensure it remains a vapor as it passes into column 201. Crude R1233zd-E stream 103 then goes to an optional water-absorber column 201, where water stream 104 is employed to remove >90% of the HF and HCl. This water-absorber column 201 may be a vapor-liquid absorber (as shown) or a liquid-liquid extractor. For this example water-absorber column 201 is a vapor-liquid absorber, using water as the absorption phase. However, a person having skill in the art can appreciate that column 201 could alternatively be a liquid-liquid extractor column, such that crude R1233zd-E stream 103 is cooled enough in the heat exchanger 301 to condense it and therefore the column is run as a liquid-liquid extractor.

In this example, water stream 104 enters the top of the column 201 and the vapor stream 103 comprising crude R1233zd-E is fed to the bottom of the water-absorber column 201. Stream 107 is the crude vapor R1233zd-E organic effluent stream from the overhead of the first column 201. Stream 107, which is vapor at this point, can be passed through optional heat exchanger 302. The optional heat exchanger 302 only cools or only heats the crude R1233zd-E stream 107, without effecting a phase change—i.e., crude R1233zd-E stream 107 remains a vapor. At this point the crude R1233zd-E stream 107 still contains small quantities of HF and HCl, and is thus taken to column 202 which is a reactor-separator. In column 202 a basic stream 106 is contacted with the crude R1233zd-E vapor stream 107. The base in stream 106 serves to remove the remaining HF and HCl from stream 107. Basic stream 106 may be for example, aqueous NaOH or aqueous KOH. The pH of stream 106 is preferably at least 10, or higher, such as at least 11 or 12 or 13 or 13.5 or close to 14.

As discussed above, a person having skill in the art can appreciate that the column 202 may be either a liquid-liquid extractor or a vapor-liquid absorber. In this example, column 202 is operated as a vapor-liquid absorber column, but if stream 107 is sufficiently cooled to a liquid in the heat exchanger 302, column 202 can be run as a liquid-liquid extractor column.

The temperature of column 202, whether run as a liquid-liquid extractor or a vapor-liquid absorber can range from 10° C. to 80° C. or from 20° C. to 70° C. or from 25° C. to 50° C., as appropriate depending on phase and temperature.

Stream 109 is the overhead from the reactor-separator column 202, which utilizes the basic stream 106. Stream 109 is therefore acid-free HCFO R1233zd-E, while stream 108, the bottoms from reactor-separator column 202 is an aqueous basic stream containing salts of HF and HCl that were removed from stream 107. Furthermore, the columns 201 (water absorber) and 202 (reactor-separator) may be a plurality of water-absorbers and/or reactor-separators. For instance, there may be none, or one or two or more water absorption columns 201, since the water-washing step is optional. There is at least one and there may be more than one reactor-separator columns 202 utilizing a stream of a base, such as NaOH, KOH, or other base such as ammonia, either alone or in combination with a reducing agent such as bisulfite, sulfite or mixtures thereof, to remove the HF or HCl from stream 101. If optional water-absorber column 201 is not used, the stream 104 is fed directly to column 202.

When operating either or both of the columns 201 or 202 as a liquid-liquid extractor, columns 201 or 202 may be any type of extraction column such as are known in the art, e.g., a Karr column, Scheibel column, packed column, or a centrifugal extractor such as a Podbielniak.

The organic rich stream 109 which is the overhead of column 202, will contain a small amount of water which may be removed by molecular sieves. The adsorption by the molecular sieves may be accomplished in the liquid or the vapor phase. The organic stream, stream 109 is then sent to downstream processing to remove lights and heavies (i.e. unwanted organics) to produce purified R1233zd-E that meets all specifications.

The aqueous streams 105 and 108, from the reactor-separator columns 201 and 202, respectively, contain about 450-500 ppm organics. Streams 105 and 108 can be sent to the wastewater purification section of the plant or streams 105 and 108 can have the organics (i.e. HFCO) removed for recycle and to reduce the environmental load of the plant. Streams 105 and 108 can be treated separately to have the organics removed or they can be combined, and the organics can be removed from the combined stream. It should be understood that the following discussion applies to either of streams 105 or 108 or a stream that is the combination of streams 105 and 108.

Figure 2:
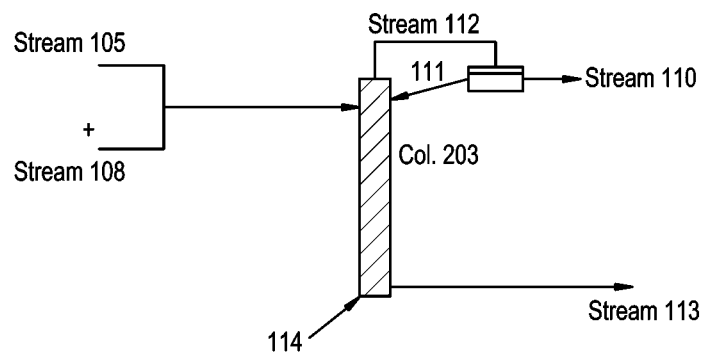
FIG. 2 shows an additional step in the process according to the invention.

A preferred way to remove the organics from these aqueous streams 105 and/or 108 is to employ a stripping column 203. FIG. 2 shows the stripping column 203. Stream 114 is the stripping agent, which can be steam, air, nitrogen or the like, with steam being preferred. The resulting aqueous stream 113, is essentially free of organics and can be disposed of in a typical fashion. The overheads from the column 203 containing the organics, stream 112, are cooled to approximately 10° C. such that the stream 112 is mostly liquid, which will cause the stream 112 to phase split into an organic-rich stream 110, which is free of HF and free of any HCl that may have been in the crude 1233zd-E, and an aqueous-rich stream 111. The aqueous stream 111 can be sent back, refluxed, into the stripping column 203 such that the water exiting the bottom of column 203 as stream 113 is essentially organic-free.

Non-limiting examples of caustic (base) stream 106 comprise 5-10 weight percent aqueous solutions of bases such as NaOH, KOH, or ammonia. The base stream 106 may further comprise reducing agents for example, but not limited to bisulfite, sulfites and mixtures thereof. The pH of stream 106 can range from 12-14, or 13-14, or 13.5-14. The temperature of stream 106 can range from 10° C.-80° C. or from 20° C.-70° C. or 30° C.-60° C. The temperature of the combined streams of 106 and 107 in column 202 can likewise range from 10° C.-80° C. or from 20° C.-70° C. or 30° C.-60° C. Likewise the temperature of the combined streams 103 and water 104 in column 201 can range from 10° C.-80° C. or from 20° C.-70° C. or 30° C.-60° C.

EXAMPLES

Laboratory experiments were performed to demonstrate that the amount of TFP generated during the reaction of crude R1233zd-E with a base is greatly reduced if the cis-(Z) isomer is removed from the crude R1233zd-E prior to the reaction with the base. The reaction with the base was also performed at various temperatures to illustrate that the removal of the cis-(Z) isomer results in a much more robust process, in terms of needing to tightly control the temperature in order to minimize the production of TFP during the reaction with a base.

All the following examples were run by feeding crude R1233zd-E having varying levels of the cis-(Z) isomer as a gas into the bottom of a 0.5 L temperature controlled glass reactor. A solution of 10% by weight KOH having pH 14 at various temperatures was recirculated from the bottom of the reactor to the top of a column filled with glass packing. The R1233zd vapor bubbled through the liquid in the reactor and then passed counter-currently through the column. The effluent crude R1233zd-E gas was dried with calcium chloride and liquefied in a liquid nitrogen trap. The composition of the liquid crude R1233zd-E before and after the reaction with the base was analyzed by gas chromatography. All concentrations of the refrigerant are shown as molar percent. The crude R1233zd comprised approximately 2 weight % HF and 0.1 weight % HCl prior to the reaction with the base.

Comparative Example 1 (not According to the Invention)

Reaction of crude R1233zd-E with 10 weight % KOH at 30° C. without prior removal of R1233zd-Z isomer. The results are shown in Table 1 below.

Feed rate of crude R1233zd-E: 4.8 g/hour
KOH solution recirculation rate: 185 mL/min

TABLE 1

Comparative Example 1 Results: Composition of crude R1233zd-E stream before and after reaction with the base, without prior removal of R1233zd-Z: (not according to the invention)

| 30° C.; R1233zd-Z NOT removed | R1233zd-Z isomer (mole %) | TFP (µmol/mol) | R1233zd-E isomer (mole %) |
|---|---|---|---|
| Before Reaction with 10% KOH | 2.34 | None detected | 95.76 |
| After Reaction with 10% KOH | 1.52 | 6517 | 95.98 |

Example 1 (According to the Invention)

In Example 1, the reaction conditions are identical to those of Comparative Example 1, except that the crude R1233zd-E stream is first distilled, to reduce the initial R1233zd-Z isomer level to 83 mol/mol. The results after the reaction with 10% KOH at 30° C. are shown below in Table 2.

TABLE 2

Example 1 Results: Composition of R1233zd stream before and after reaction with the base, with prior removal of R1233zd-Z: (according to the invention)

| 30° C.; R1233zd-Z removed | R1233zd-Z isomer (µmol/mol) | TFP (µmol/mol) | R1233zd-E isomer (mole %) |
|---|---|---|---|
| Before Reaction with 10% KOH | 83 | None detected | 99.97 |
| After Reaction with 10% KOH | 123 | 29 | 99.96 |

Comparative Example 2: (not According to the Invention)

Reaction of crude R1233-E with 10 weight % KOH at 50° C. without prior removal of R1233zd-Z isomer. The results are shown in Table 3 below.

Feed rate of crude R1233zd-E: 6.2 g/hour
KOH solution recirculation rate: 185 mL/min

TABLE 3

Comparative Example 2 Results: Composition of crude R1233zd-E stream before and after reaction with the base, without prior removal of R1233zd-Z isomer: (not according to the invention)

| 50° C.; R1233zd-Z NOT removed | R1233zd-Z isomer (mole %) | TFP (µmol/mol) | R1233zd-E isomer (mole %) |
|---|---|---|---|
| Before Reaction with 10% KOH | 2.30 | None detected | 95.81 |
| After Reaction with 10% KOH | 1.38 | 6553 | 96.11 |

Example 2 (According to the Invention)

In Example 2, the reaction conditions are identical to those of Comparative Example 2, except that the crude R1233zd-E stream is first distilled, to reduce the initial R1233zd-Z level to 38 µmol/mol. The results after the reaction with 10% KOH at 50° C. are shown below in Table 4.

TABLE 4

Example 2 Results: Composition of crude R1233zd-E stream before and after reaction with the base, with prior removal of R1233zd-Z isomer: (according to the invention)

| 50° C.; R1233zd-Z removed | R1233zd-Z isomer (µmol/mol) | TFP (µmol/mol) | R1233zd-E isomer (mole %) |
|---|---|---|---|
| Before Reaction with 10% KOH | 38 | 1 | 99.98 |
| After Reaction with 10% KOH | 48 | 22 | 99.98 |

These results shown in the Examples and Comparative Examples illustrate that when the crude R1233zd-E is distilled to remove the R1233zd-Z isomer prior to the reaction with the base, that the production of TFP is significantly reduced compared to the same reaction without removing the R1233zd-Z isomer. Additionally, the amount of R1233zd-E isomer is essentially unchanged after the reaction with the base. Further, the production of TFP is not increased by reacting the base with the crude R1233zd-E at a higher temperature, if the R1233zd-Z isomer is removed prior to contacting the crude R1233zd-E stream with the base.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

What is claimed is:

1. A method for the removal of an acid, wherein the acid comprises at least one of HF or HCl, from a crude stream of a hydrochlorofluoroolefin (HFCO) wherein the HFCO comprises at least one E isomer and at least one corresponding Z isomer, wherein the method comprises the steps of:
    a) reducing the amount of one of the E isomer or the corresponding Z isomer in the crude stream of an HFCO to produce a reduced isomer crude HFCO stream;
    b) contacting the reduced isomer crude HFCO stream with an aqueous base stream, wherein step b) takes place at a reaction temperature;
        whereby the base reacts with the at least one of HF or HCl forming a salt, whereby the removal of at least one of HF or HCl is accomplished by removal of the salt and wherein step b) produces a reduced isomer reduced acid crude HFCO stream and a basic aqueous trace crude HFCO stream comprising the salt;
    wherein step a) is performed prior to step b).

2. The method according to claim 1, wherein the crude stream of a hydrochlorofluoroolefin comprises E (trans)-1,1,1-trifluoro-3-chloro-2-propene and Z (cis)-1,1,1-trifluoro-3-chloro-2-propene and the step a) comprises reducing the amount of Z (cis)-1,1,1-trifluoro-3-chloro-2-propene in the crude stream of the hydrochlorofluoroolefin.

3. The method according to claim 1, wherein step a) comprises a step of distillation.

4. The method according to claim 1, wherein the aqueous base stream has a pH of at least 13.5.

5. The method according to claim 1, wherein the aqueous base stream comprises at least 5 weight % aqueous KOH or at least 5 weight % NaOH.

6. The method according to claim 1, wherein the reaction temperature is 50° C. or less.

7. The method according to in claim 1, wherein the reaction temperature is 30° C. or less.

8. The method according to claim 1, further comprising a step c), wherein step c) is performed after step a) and prior to step b); wherein step c) comprises a step of contacting the reduced isomer crude HFCO stream with a water stream whereby the water stream dissolves the at least one of HF or HCl, whereby partial removal of at least one of HF or HCl is accomplished, wherein step c) produces an aqueous HF/HCl/trace crude HFCO stream and a reduced acid crude HFCO stream and wherein the reduced acid crude HFCO stream is fed to step b) and wherein step c) takes place at a washing temperature.

9. The method according to claim 1 wherein the method further comprises a step d) wherein step d) is accomplished after step b), and wherein the step d) comprises a step of removing trace crude HFCO from the basic aqueous trace crude HFCO stream emerging from step b).

10. The method according to claim 9, wherein step d) comprises stripping using a stripping agent and wherein the stripping agent is selected from the group consisting of air, nitrogen, and steam.

11. The method according to claim 10, wherein the stripping agent comprises steam.

12. The method according to claim 8, wherein the method further comprises a step e) wherein the step e) is accomplished after step b) and after step c), and wherein step e) comprises i) combining the basic aqueous trace crude HFCO stream emerging from step b) with the aqueous HF/HCl/trace crude HFCO stream emerging from step c) to produce a combined aqueous trace crude HFCO stream and ii) removing trace crude HFCO from the combined aqueous trace crude HFCO stream.

13. The method according to claim 12, wherein ii) comprises stripping using a stripping agent and wherein the stripping agent is selected from the group consisting of air, nitrogen, and steam.

14. The method according to claim 13, wherein the stripping agent comprises steam.

15. The method according to claim 1, wherein the reduced isomer reduced acid crude HFCO stream emerging from step b) comprises less than 3000 µmol/mol of 3,3,3-trifluoropropyne.

* * * * *